United States Patent [19]
Koivukangas et al.

[11] Patent Number: 4,834,089
[45] Date of Patent: May 30, 1989

[54] ADAPTER FOR BRAIN SURGERY

[76] Inventors: John P. Koivukangas, Solkitie 7, SF-90250 Oulu; Seppo V. Noponen, Mastolantie 5 as. 2, SF-90230 Oulu, both of Finland

[21] Appl. No.: 86,691
[22] PCT Filed: Dec. 1, 1986
[86] PCT No.: PCT/FI86/00139
  § 371 Date: Jul. 13, 1987
  § 102(e) Date: Jul. 13, 1987
[87] PCT Pub. No.: WO87/03190
  PCT Pub. Date: Jun. 4, 1987

[30] Foreign Application Priority Data
  Feb. 12, 1985 [FI] Finland .................. 854751

[51] Int. Cl.⁴ ............................................ A61B 17/00
[52] U.S. Cl. ................................ 128/303 R; 604/175
[58] Field of Search ............... 128/303 R, 303 B, 345; 604/175

[56] References Cited
U.S. PATENT DOCUMENTS

| | | | |
|---|---|---|---|
| 1,398,842 | 11/1921 | Cruse | 128/303 B |
| 2,480,737 | 8/1949 | Jayle | 128/305 |
| 3,016,899 | 1/1962 | Stenvall | 604/175 |
| 3,021,842 | 2/1962 | Flood | 604/175 |
| 3,053,256 | 9/1962 | Cooper et al. | 128/303 R |
| 3,115,140 | 12/1963 | Volkman | 128/303 B |
| 3,135,263 | 6/1964 | Connelley, Jr. | 128/303 B |
| 3,263,683 | 8/1966 | Vddenberg | 128/303 R |
| 3,384,086 | 5/1968 | Rocha-Miranda et al. | 128/303 B |
| 3,508,552 | 4/1970 | Hainault | 128/303 B |
| 3,817,249 | 6/1984 | Nicholson | 128/303 B |
| 4,058,114 | 11/1977 | Soldner | 128/303 B |
| 4,206,763 | 6/1980 | Pedersen . | |
| 4,485,819 | 12/1984 | Igl . | |
| 4,542,747 | 9/1985 | Zurinski . | |
| 4,602,622 | 7/1986 | Bar et al. | 128/303 B |
| 4,608,977 | 9/1986 | Brown | 128/303 B |
| 4,638,798 | 1/1981 | Shelden et al. | 128/303 R |
| 4,688,570 | 8/1987 | Kramer et al. | 128/303 R |

FOREIGN PATENT DOCUMENTS
A20030355 12/1980 European Pat. Off. .

Primary Examiner—John D. Yasko
Attorney, Agent, or Firm—Ladas & Parry

[57] ABSTRACT

The invention relates to a neurosurgical auxiliary apparatus or a brain surgery adapter (150) for neurosurgical procedures carried out through a craniotomy opening, such as imaging and/or tumor resection. The brain surgery adapter (150) comprises an adapter frame (30) arranged to be clamped and sealed (20) to the edges of the craniotomy opening (6); a preferably turnable imaging plate (70) which comprises a slide space and which is arranged to be fitted in the frame and locked in position; and an ultrasonic transducer (120) which is fitted in a transducer socket (110) provided in the slide space of the imaging plate. When the adapter according to the invention is used, the ultrasonic transducer need not be supported manually. The adapter defines a closed liquid space, and it can also be provided with instruments for performing a neurosurgical operation, such as tumor resection. Imagings are carried out by means of the brain surgery adapter according to the invention in a determined imaging plane and the obtained images are accurately determined and comparable with each other irrespective of the fact that the tissue adapts itself during the tumor resection.

14 Claims, 5 Drawing Sheets

FIG. 8
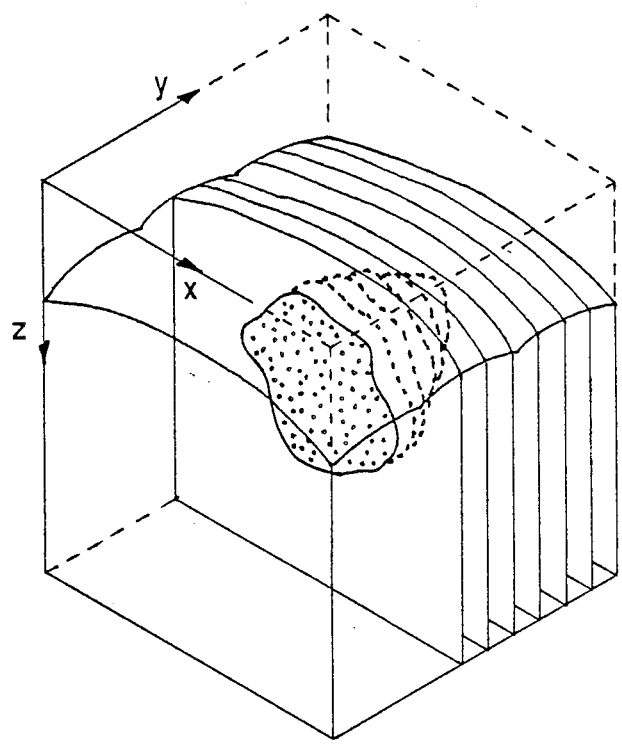
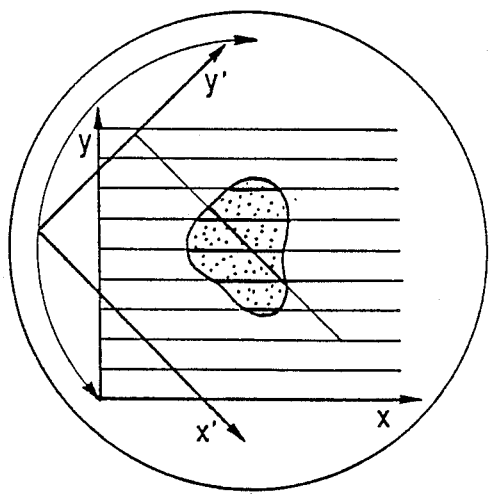
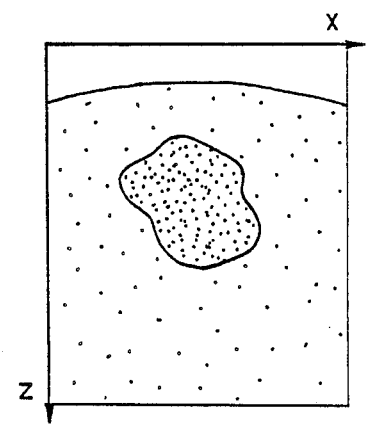
FIG. 9
FIG. 10

ADAPTER FOR BRAIN SURGERY

The invention relates to a neurosurgical auxiliary apparatus for use in brain operations, i.e. a brain surgery or brain imaging adapter intended for surgical procedures performed through a craniotomy opening, for imaging and/or tumor resection; the adapter comprising an ultrasonic transducer, means for supporting the transducer, and means for introducing medium into the craniotomy opening. By means of the adapter the operating neurosurgeon obtains a three-dimensional determination of the shape and position of a tumor to be removed, for instance. Imaging is carried out by means of the ultrasonic transducer. The adapter according to the invention is the first stereotactic apparatus for tumor resection which is attached to the skullbone and which at the same time functions as an imaging apparatus, being provided with the ultrasonic transducer. Surgical instruments may also be attached to the adapter.

Known methods for the determination of a tissue object to be removed include x-ray CT imaging and NMR imaging, which can be used preoperatively and under certain conditions even intraoperatively (Lunsford, L. D., R. Parrish and L. Albright (1984) Intraoperative imaging with a therapeutic computed tomographic scanner, Neurosurgery 15: 559–561). Intraoperative ultrasound determination can be carried out either with a sector or a linear transducer, the imaging being performed through a craniotomy opening into which medium has been introduced (Koivukangas J. (1984) Ultrasound imaging in operative neurosurgery: An experimental and clinical study with special reference to ultrasound holographic B (UBH) imaging, Academic dissertation, Acta Universitatis Ouluensis, Series D, Medica No. 115, Neurologica et Neurochirurgica No. 10). When a known apparatus is used, the operating surgeon performs the imaging from a desired direction, supporting the detector manually or by means of a separate supporting apparatus (Tsutsumi Y., Y. Andoh and N. Inoue (1982) Ultrasound-guided biopsy for deep-seated brain tumors, J. Neurosurg. 57: 164–167). In this way it is possible to roughly determine the position and shape of a tumor located e.g. under intact tissue. On the basis of this information the surgeon can decide the position and direction of the tissue incision. After the incision, the removal of the tumor can be carried out by means of some known method.

One problem with known apparatuses is that the operating neurosurgeon has to support manually the ultrasonic transducer; that the precise location and shape of the object cannot be determined; and that the imaging cannot be accurately repeated. The distance of the tumor from the surface of the brain can be determined accurately from a high-quality ultrasound image, whereas the transfer of the information from the image to the object is difficult, because there is no accurate data on the place and orientation of the imaging plane. Further, the precise border of the tumor to intact tissue cannot necessarily be visually determined in the incised tissue, even though it may be visible in an ultrasound image. Since all tumors are not accurately visualized in an x-ray CT image, either, intraoperative ultrasound imaging is of great importance. After resection of the tumor or a part thereof, the tissue adapts itself and changes shape so that the imaging has to be repeated for the determination of the new location and shape. The problems are repeated, too, and the images are not comparable with each other. Tissue spatulas or hollow tubes generally used in operations have to be supported on the edge of the patient's craniotomy opening, a stereotactic frame or some other separate support by means of flexible arms which can be locked in position. The position and massiveness of the tissue supports hampers the intraoperative ultrasound imaging, because the shadow regions and reflections created thereby are difficult to avoid.

For imaging, the ultrasonic transducer requires contact with the brain tissue, either directly or through a medium, such as saline solution, which transmits the acoustic wave to the tissue and the echo back therefrom. With known apparatuses, the handling of the medium is difficult, because the position of the patient's head may be different in different operations. Attempts have been made to avoid the problem by the use of a liquid bag or a plastic film which is positioned between the transducer and the tissue. However, plastic or rubber sheets and the like hamper the acoustic wave and thus deteriorate the quality of the image and may cause the image to be distorted.

A further disadvantage of known apparatuses is that they do not generally allow the neurosurgeon to repeatedly determine the location of a certain point within the brain tissue during the operation, because there is no coordinate plane in which the location of the point could be determined and measured. This is a serious drawback especially in the resection of irregularly defined tumors.

By means of the apparatus according to the invention, a decisive improvement is obtained with respect to the above disadvantages. The invention is characterized by what is disclosed in the claims.

The most important advantage of the invention is that the accurate position and shape of a brain tumor, for instance, can be repeatedly determined in relation to a fixed reference plane with respect to which a set of coordinates is assumed to be positioned. In the apparatus according to the invention, the ultrasonic transducer is provided with a socket so that one does not have to support the transducer manually. The transducer can be turned in the socket by means of an imaging plate to find a suitable imaging direction. By turning a transducer positioned in place around its central axis during imaging, a series of ultrasonic images is obtained by means of which the object can be determined in a set of circular or spherical coordinates. Being positioned on an imaging slide, the transducer is also linearly movable, so that the tumor can be imaged and determined at regular intervals in sufficiently thin slices. The displacements can be made simply and precisely by means of a displacing lever or some other actuator. When assembled, the brain surgery adapter defines a closed liquid space, which simplifies the imaging, because the patient's head can be placed in a position most advantageous for the operation, and no separate bags or films are needed for obtaining the liquid space. The liquid is easy to handle, since it can be tapped from a storage bottle in a sterile manner and discharged through a discharge hose after the conclusion of the imaging. Since the craniotomy opening of the patient can be directed as desired, air bubbles contained in the liquid rise to the top, so they do not obscure the imaging. Liquid for a repeated imaging can be provided rapidly after the imaging plate has been positioned in place. Repeat images can be appreciated in comparison with the previous ones, because the imagings can, if desired, be performed accurately from the same place and direction.

The brain surgery adapter is clamped directly to the edge of the craniotomy opening, i.e. a skull seal corresponding to the sealing plate provided on the underside of an adapter ring is pressed against the edge of the craniotomy. The sealing plate is separate and the skull seal provided thereon is fitted in place so that it follows the edges of the craniotomy opening. In this way the adapter can be clamped and sealed to craniotomy openings of various sizes and shapes; further, the position of the craniotomy may vary to a great extent.

Skull fastening ribs, spatula shafts, instrument supports, hose couplings, etc., can be fitted in the shaft holes of the adapter frame. The shafts can be oriented and locked in a given place and position. The auxiliary devices fitted in the shaft holes can be stationary during the imagings so that intraoperative changes in the tissue configuration are reduced. Auxiliary devices may also pass over the instruments and act as probes, even concurrently with the imaging. Consequently, the imaging can be provided with dynamic observation so that two tissue types, for instance, can be compared with each other for the identification of tumor tissue. Tubular brain tissue supports can also be clamped to the adapter frame.

When the apparatus according to the invention is used, the auxiliary devices clamped to the adapter frame take only a little room so that the neurosurgeon has plenty of room for the operation. Safety is improved, because spatulas with long shafts or arms which might damage intact brain tissue are not needed.

Sterilizing problems are reduced by the use of the brain surgery adapter, because no separate plastic sheets, for instance, are needed for the contact material of the transducer and because the liquid space is closed. Thus fewer impurities contained in the air, for instance, get into the brain tissue.

Tumor resection is easier to perform, since the adapter frame provides support for the surgeon's hands so that movements become more exact. At the same time the hand does not tire to such an extent as previously and operative accuracy is improved.

By virtue of the brain surgery adapter, the operation time is shorter than previously, because repeated tissue removals, for instance, are direct continuations of the previous ones, and the objects need not be relocalized and redetermined. This provides a considerable reduction in costs and the clinical strain of the patient is reduced, which, in turn, speeds up the postoperative treatment.

In the following the invention will be described in detail with reference to the attached drawings.

FIG. 8 illustrates schematically planes within a tumor area as shown in a certain set of coordinates.

FIG. 9 illustrates schematically individual imagings performed in two different directions.

FIG. 10 illustrates one individual image in which a slice of tumor is visible.

Figure 1:
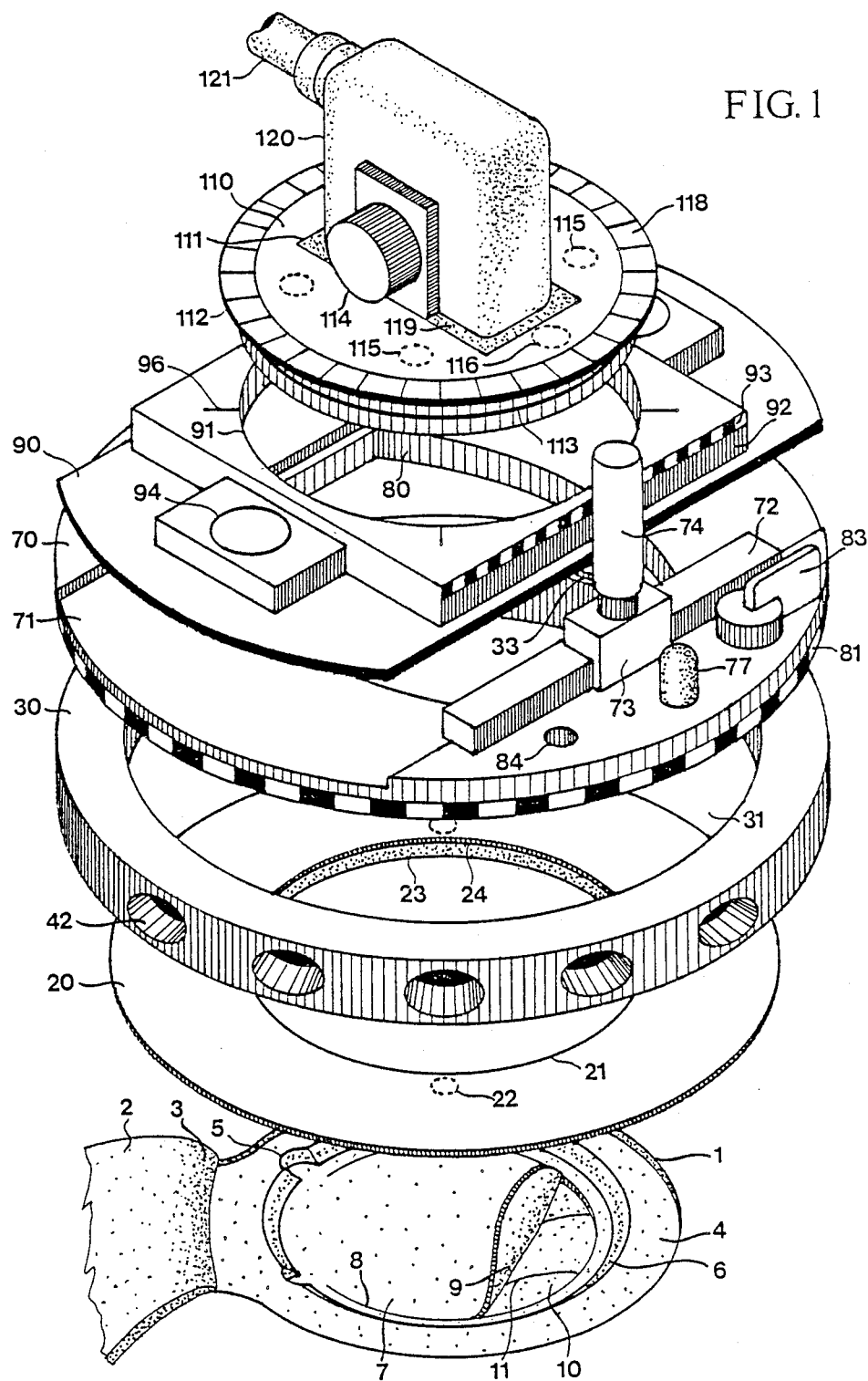
FIG. 1 illustrates the assembling order of the components of the brain surgery adapter from below upwards.

A scalp incision 1 is shown at the bottom in FIG. 1. The scalp 2 is turned aside from the incision with a fold 3. Holes 5 are bored in the skullbone 4 for craniotomy, and the edge of the craniotomy opening 6 between the holes is sawed so as to make it slanted in order that the bone flap to be positioned in place after the operation would not press the dura 7. A dural incision 8 is nearly as large as the craniotomy opening, the size of which, in turn, is of the same order as the size of an operative opening 21 of a sealing plate 20. Under the dura turned aside 9, the cortex 10 is visible and convolutions 11 are seen on the cortex. The tumor to be removed is positioned somewhere within the skull, in the white matter of the brain, for instance.

The sealing plate 20 positioned above the craniotomy opening fits tightly in a fitting groove 33 provided on the underside of an adapter frame 30. A skull seal 23 of suitable shape is fastened on the lower surface of the plate 20 at the edge of the operative opening 21 in such a way that it also follows the edges of the craniotomy opening 6. The skull seal is manufactured of suitable cellular rubber material resistant to sterilizing by casting into suitable dimensions and shape. The skull seal 23 is attached to the lower surface of the sealing plate 20 e.g. by means of an adhesive layer 24. If the sealing plate 20 is fastened directly to the craniotomy opening 6, this is carried out by means of screws inserted into holes 22.

Figure 6:
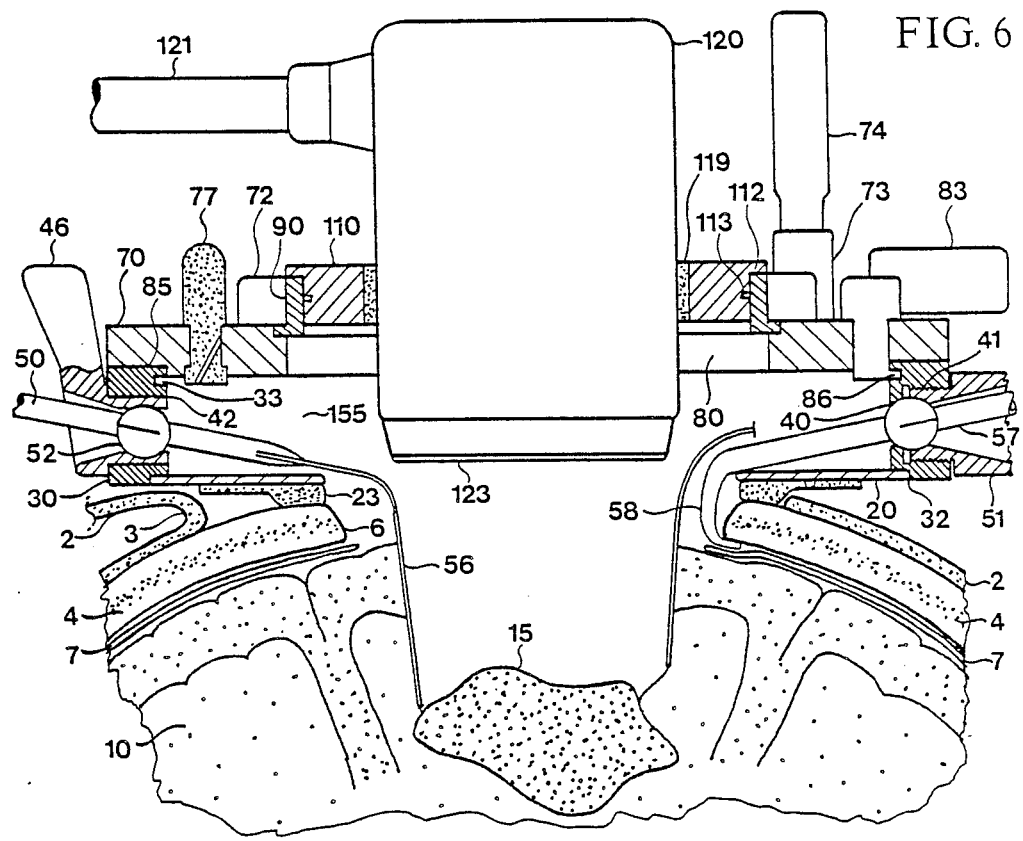
FIG. 6 is a partial sectional side view of the brain surgery adapter clamped to the skull and ready for imaging.

The adapter frame 30 shown in FIG. 1 above the sealing plate 20 is provided with shaft holes 42 which in FIG. 1 have a mutual spacing of 30 degrees and are provided with friction surfaces for friction locking by means of which the shafts are locked in place. The shaft holes 42 may also be provided with threadings in which case they are locked by means of locking nuts. A locking groove 33 (shown in FIG. 6) is provided on the edge of an instrument space 31 of the adapter frame 30 for the eccentrics 86 of turn latches 83 of the imaging plate (FIG. 6). The locking groove 33 may also be used for the fastening of additional instruments.

The underside of the imaging plate 70 shown above the adapter frame 30 is provided with a fitting groove for the adapter frame 30. The imaging plate 70 comprises a slide space 71 and an imaging aperture 80. The imaging plate 70 can be turned upon the adapter frame 30 without any obstacle; it can be fastened as well as locked in any desired position by means of turn latches 83 which are preferably four in number and which are mounted in turn latch holes 84. A slide bar 72 formed on the edge of the slide space 71 comprises a movement mechanism 73 provided with a displacing lever 74 for moving an imaging slide 90. By means of the mechanism 73, the imaging slide 90 can be moved accurately and locked in a certain position. The outer periphery of the imaging plate 70 is provided with a scale 81 for determining the imaging direction. Both edges of the imaging plate 70 are provided with air removal valves 77 through which air is released from the liquid space when the space is filled up.

The imaging slide 90 shown above the imaging plate 70 in FIG. 1 fits in the slide space 71 of the imaging plate 70. The imaging slide 90 is provided with a space 91 for the socket of the transducer and with a socket locking means 94. A displacing cogging 92 is formed on the edges of the imaging slide 90 for the linear movement of the imaging slide 90 between the different individual imagings. Cog extensions 93 function as a scale by means of which the position of the individual images is determined. Turning marks 96 function as indicators of the turning of the transducer. The imaging slide 90 can be detached entirely or turned aside during the operative procedure.

A transducer socket 110 comprises a transducer seal 119 positioned in a transducer opening 111, the seal 119 being intended for supporting and sealing various kinds of transducers. A socket shoulder 112 seals the transducer socket 110 against the edge of the socket opening 91 of the imaging slide 90. The transducer socket 110 is provided with a socket groove 113 cut into its periphery for the turning and locking of the transducer. The transducer is locked in place by means of a transducer locking means 114. The vertical position of the transducer 120 in the socket 110 is adjustable so that the distance of the imaging objects from the coordinate plane can be correspondingly varied in the imaging. The holes 115 are provided for the mounting of additional devices and instruments. A hole 116 is provided for a biopsy forceps guide provided with a ball joint which can be locked. The biopsy line is thereby located in the image plane. A socket scale 118 is provided on the edge of the transducer socket 110, by means of which scale the turning of the transducer 120 can be observed in a set of spherical coordinates.

The transducer 120 mounted in the transducer socket 110 is an ultrasonic linear or sector transducer. A cable 121 connects the transducer 120 to the imaging apparatus.

Figure 2:
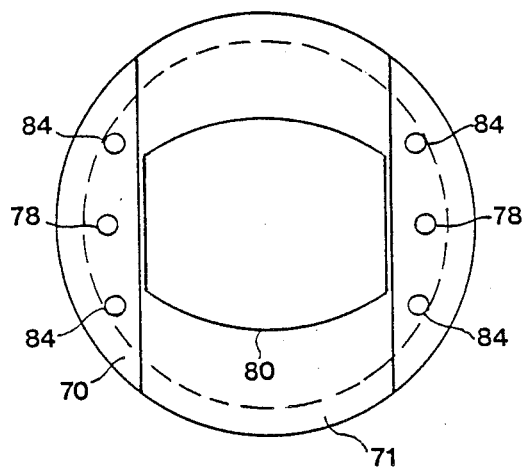
FIG. 2 illustrates an imaging plate provided with an imaging aperture.

FIG. 2 shows the slide space 71 provided in the imaging plate 70, holes 78 for the air removal valves and holes 84 for the turn latches. The figure also shows the imaging aperture 80.

Figure 3:
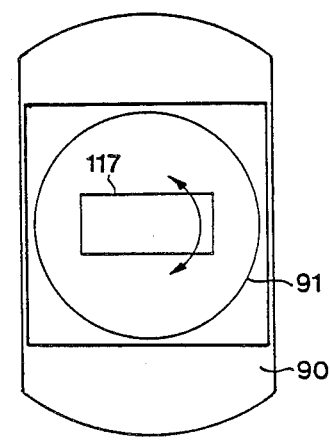
FIG. 3 illustrates an imaging slide to be fitted in the imaging plate.

FIG. 3 shows the space 91 provided in the imaging slide 90 for the transducer socket 110. A rectangle 117 drawn in the figure illustrates the position of the transducer and the arrows illustrate the turning of the transducer with the transducer socket attached to the imaging slide.

Figure 4:
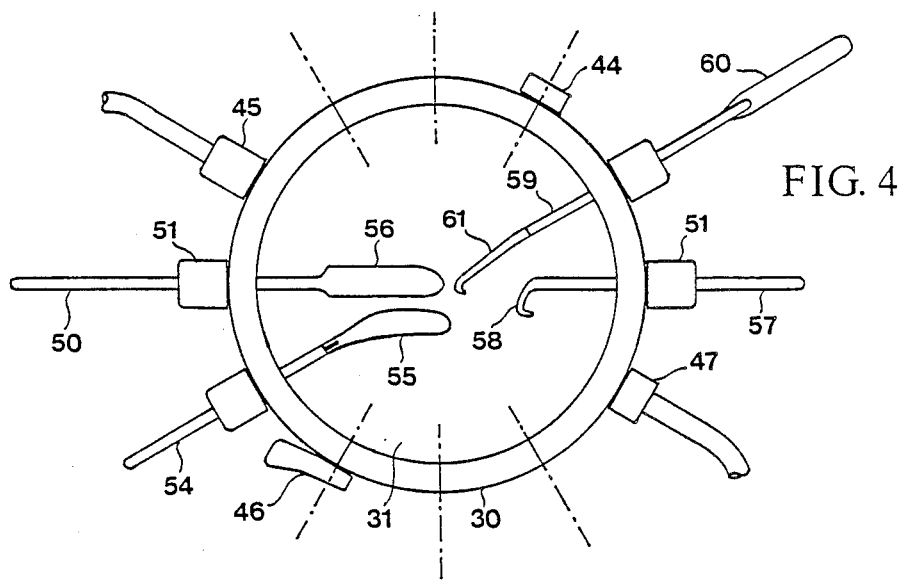
FIG. 4 illustrates the positioning of instruments within the adapter structure.

FIG. 4 shows a few shafts and other components clamped within the adapter frame 30 at regular intervals of 30 degrees. A shaft 50 is provided with a flexible tissue spatula 56 and it can be entirely inserted into the shaft hole of the adapter frame 30 and locked at a suitable position after it is oriented and placed in position. A jointed shaft 54 is provided with a spatula 55 which can be positioned in a desired position. A shaft 57 provided with a skull fastening rib 58 is inserted into the shaft hole from within the adapter frame 30, and is clamped by drawing from outside the frame, whereafter it is locked in place. Alternatively, the adapter frame 30 can be secured to the operating table by means of some other supporters. In this way it is easier to position the other apparatuses needed in the operation, and the interaction of the apparatuses is made possible. A rigid instrument shaft 59 is provided with a handle 60 and its point 61 may be, in real-time imaging, for instance, a tissue hook, an imaging mark or some other detachable instrument. The locking of the shafts is carried out either with a locking nut 51 or a friction locking means 46. The fixing of the shafts of the brain surgery adapter may also be rigid instead of adjustable. The adapter frame 30 is provided with a filling connection 45 and a discharge connection 47 for the liquid. A closing plug 44 prevents the liquid from flowing out through empty shaft holes.

Figure 5:
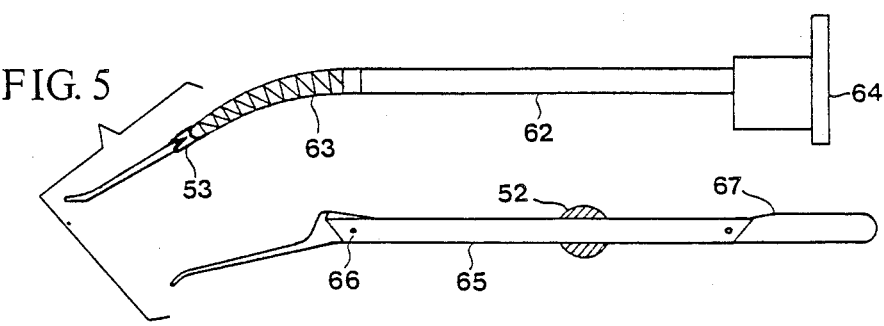
FIG. 5 illustrates shaft and instrument models which can be fitted in the adapter frame and locked in place.

FIG. 5 shows two specific tissue supports. A shaft 62 is provided with a flexible part 63 and it can be locked at a desired angle by means of a locking disc 64. The flexible shaft portion may be provided with gripping tweezers 53 in which case the spatula is replaceable. A shaft 65 is provided with a joint 66. The joint may also be replaced with gripping means for various kinds of auxiliary devices. FIG. 5 shows a ball joint 52 and locking means 67 for locking the joint 64.

FIG. 6 shows a brain surgery adapter 150 when it is assembled, mounted in place and ready for imaging. The adapter 150 is clamped to the edge of the craniotomy opening 6 by means of the skull fastening rib 58, for instance. The dura 7, the brain tissue 10 and the tumor 15 are shown in the figure. The brain tissue 10 is retracted from the tissue incision and supported by means of the spatula 56 so that the tumor 15 becomes visible. The scalp 2 has been removed from the area of the craniotomy opening and turned aside with a loose fold 3. The skull seal 23 positioned upon the skullbone 4 is attached to the sealing plate 20, which, in turn, is tightly fitted in the fitting groove 32 of the adapter frame 30. The adapter frame 30 comprises an unthreaded shaft hole 42 for the friction locking means 46. The ball joint 52 is visible within the shaft hole 42, which ball joint locks in position the shaft 50 going through the hole. The shaft hole 40 on the opposite side of FIG. 6 is provided with a locking threading 41 into which the locking nut 51 is screwed so that the shaft 57 of the skull fastening rib will be locked in place by means of the ball joint. The imaging plate 70 positioned upon the adapter frame 30 is locked in place by means of the eccentrics 86 of the turn latches 83 from the locking groove 33 of the adapter frame. The imaging slide 90 positioned above the imaging aperture 80 of the imaging plate 70 is supported stationary by means of the slide bars 72, and it is moved by means of the displacing mechanism 73 and the displacing lever 74. The imaging plate 70 further comprises the air removal valve 77 and the fitting groove 85 of the adapter frame. The transducer socket 110 fitted in the imaging slide comprises not only the shoulder 112 but also the socket groove 113, which is used as an aid in the locking. The transducer seal 119 positioned in the transducer opening of the socket 110 supports the ultrasonic transducer 120, which is further locked in place by means of the transducer lock. An element matrix 123 of the lower portion of the ultrasonic transducer 120 is directed to the imaging object. The cable 121 connects the transducer 120 to the other parts of the imaging apparatus. The brain surgery adapter thus defines a closed liquid space 155 the upper surface of which does not need to be horizontally positioned for the imaging.

Figure 7:
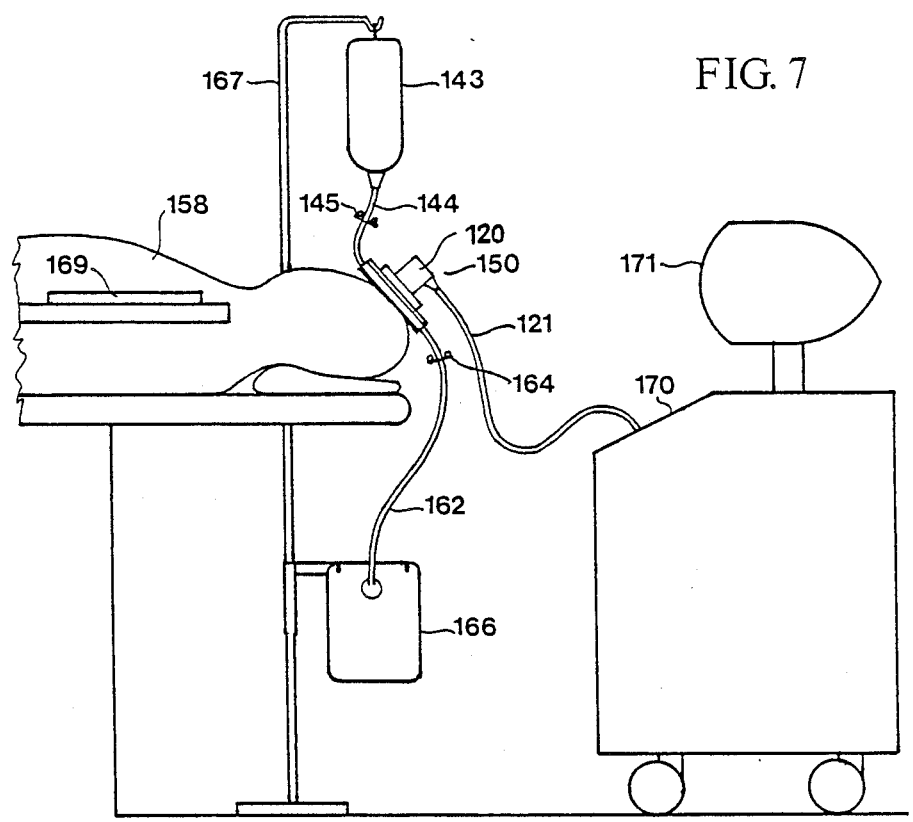
FIG. 7 illustrates the operation system during brain surgery.

FIG. 7 illustrates the intraoperative operation arrangement. The brain surgery adapter 150 is connected to the craniotomy opening of a patient 158. A liquid bottle 143 suspended from a supporting rack 167 is at a suitable height for creating a slight pressure in the filling hose 144, which is provided with a closing spring 145. The discharge hose 162 passes freely downwards into an emptying bag 166. The discharge hose 162 is provided with an emptying spring 164. During imaging intervals the imaging plate can be turned aside or it can be placed on a platform 169 shown in the figure where it stays sterile. The cable 121 connects the transducer 120 to the other parts of the imaging apparatus 170, the monitor 171 of which is positioned suitably in view of the operation.

FIG. 8 illustrates schematically planes or individual images within the tumor area in a certain set of coordinates. These individual images provide a three-dimensional determination of the tumor and its location. The individual images are comparable with x-ray CT and NMR images, and they can be used for controlling and observing the operation. The individual images can be positioned in a determined set of x-y-z -coordinates or, if the imagings are carried out by turning the transducer around the central axis, the individual images are positioned within circular or spherical coordinates so that it is also possible to localize the extent of the outer dimensions of the tumor solely by means of the adapter frame.

FIG. 9 illustrates the possibility of performing imagings from different directions by turning the imaging plate. This is necessary, if an irregularly defined tumor is to be imaged during operation, for example.

FIG. 10 illustrates schematically one individual image, from which the dimensions of the tumor can be measured in a given plane.

The craniotomy opening 6 of FIGS. 1 and 6 is made by known methods after the optimum resection site of the tumor has been determined by x-ray CT or other such imaging. The scalp incision is made slightly larger than the craniotomy so that the skull seal 23 can be positioned within the area between the edge of the scalp and that of the skullbone. The incised scalp is drawn aside sufficiently and fixed so that the adapter frame would not press it. The craniotomy opening 6 is positioned on the basis of the preoperative data in such a manner that the tumor is located in the middle of the imaging area as viewed from the operative direction so that the tissue incision can be performed within the central area in such an extent as required. It is also possible to control an operation carried out in an oblique direction by means of the apparatus. The dural incision 8 is performed in a normal way and the dura is drawn aside and fixed. The adapter frame 30 is positioned upon the sealing plate 20 fitted in the craniotomy opening 6 and it is fixed either directly to the skullbone 4 by means of screws or to the edges of the craniotomy opening by means of the skull fixing ribs, the straight end portions of which are inserted through the shaft holes from within the adapter frame 30 at suitable positions to be mounted therein. The skull fixing ribs are locked by means of the ball joint and the locking nut by turning these into the corresponding shaft holes. Since the tissue incision has not been carried out during the first imaging, it is not necessary to position the spatulas within the frame, so the closing plugs 44 of rubber are inserted into the open shaft holes in order to prevent the liquid from flowing out. Hoses 144 and 162 are positioned in two of the shaft holes for filling the liquid space and for discharging liquid respectively. The hoses are provided with plug-like clamps. The discharge hoses 162 and the filling hoses 144 are provided with spring compressors 145, 164 which function as taps. Then the transducer 120 is positioned in the transducer socket 110, and the transducer with the socket and the imaging slide 90 are mounted in position in the imaging plate 70 and the imaging plate is locked by means of the turn latches 83 to the adapter frame 30, the liquid space can be filled with a saline solution for the imagings. When the discharge hose 162 is closed, one air removal valve 77 is drawn into the upper position and liquid is tapped from the suspended bottle 143 by opening the closing spring 145 until the liquid starts to flow out of the air removal valve 77, which is closed immediately. The liquid space 155 is kept filled with liquid. The brain surgery adapter 150 is now ready for imaging. After a suitable imaging line is found, the imaging plate 70 can be locked in a determined position and the value of the slide scale 94 is written down and the individual images can be taken by intermittently pressing the slide displacing lever 74, continually observing the slide scale 93. In this way such a three-dimensional determination of the object as shown in FIG. 8 is obtained, by means of which the tumor can be detected, identified and removed. The first tissue incision is made on the basis of this determination, the tumor being visible in the incision, provided that it is distinguishable from the surrounding tissue. Information obtained by means of ultrasound imaging can be utilized e.g. for controlling tissue destructing devices based on laser or ultrasound.

An auxiliary device to be attached to the adapter frame may be a measuring device comprising several degrees of freedom which can be used for obtaining measuring results of various kinds from the tissue incision and also for transferring measuring results information to the tissue incision.

We claim:

1. A brain surgery adapter for a neurosurgical procedure carried out through a craniotomy opening, such as imaging, tumor resection or the like, the adapter comprising:
   an adapter frame to function as a determination plane for the neurosurgical procedure;
   means for fastening the adapter frame to the skull to envelope the craniotomy opening;
   seal means provided between the adapter frame and the skull for sealing the adapter frame in a liquid-proof manner to the skull; and
   supporting means for neurosurgical instruments, such as imaging means, operating means or the like, to be fastened to the adapter frame in a liquid-proof manner in order to define with the imaging means a closed space fillable with liquid.

2. An adapter according to claim 1, wherein the seal means comprises a skull seal to be placed against the skull and a sealing plate provided between the adapter frame and the skull seal.

3. An adapter according to claim 1 wherein
   the adapter frame is provide with borings or shaft holes; and
   the means for fastening the adapter frame to the skull comprises shafts having two ends, one end of each shaft being fitted in one of said shaft holes of the adapter frame, the other end of each shaft being bent to be fastened to edges of the craniotomy opening to clamp the adapter frame to the skull.

4. An adapter according to claim 3 wherein the shaft holes of the adapter frame are provided with ball joints through which the shafts are brought in order to direct and lock the same.

5. An adapter according to claim 4 wherein the ball joint comprises a locking nut for locking the ball joint.

6. An adapter according to claim 4, wherein the ball joint comprises a friction locking means for locking the ball joint.

7. An adapter according to claim 1 wherein the adapter frame is provided with a locking structure for fastening the supporting means to the adapter frame in a liquid-proof manner and the supporting means of the imaging means comprise an imaging plate having a round circumference.

8. An adapter according to claim 7 wherein the locking structure for the imaging plate comprises a locking groove in the adapter frame, said groove enabling turning of the imaging plate before it is locked in a desired position.

9. An adapter according to claim 8 wherein the imaging plate is provided with a slide space in which an imaging slide is arranged to be slidably fitted, the imaging plate and the imaging slide having mutual slide surfaces.

10. An adapter according to claim 9 wherein the imaging slide is provided with a round transducer socket space extending through the imaging slide in which space a neurosurgical instrument, such as an imaging means, e.g. an ultrasonic transducer, an operating means or the like or a socket therefor is arranged to be turnably and lockably fitted.

11. An adapter according to claim 1 wherein the supporting means is provided with at least one air removal valve for releasing air through the supporting means from said closed space to the atmosphere when said closed space is filled with liquid.

12. An adapter according to claim 7 wherein the imaging plate is provided with actuating means, such as a displacing mechanism, for moving the imaging slide and for locking it in place.

13. An adapter according to claim 7 wherein the imaging plate is provided with a scale on the circumference thereof for defining the turning position of the imaging plate relative to the adapter frame.

14. An adapter frame according to claim 9 wherein the imaging slide is provided with a slide scale provided on at least one of the slide surface of the imaging slide for defining the position of the imaging slide relative to the imaging plate.

* * * * *

UNITED STATES PATENT AND TRADEMARK OFFICE
CERTIFICATE OF CORRECTION

PATENT NO.  : 4,834,089
DATED       : MAY 30, 1989
INVENTOR(S) : John P. KOIVUKANGAS It is certified that error appears in the above-identified patent and that said Letters Patent is hereby corrected as shown below:

On the title page, Item [30] "February 12, 1985"

should read -- December 2, 1985 --

Signed and Sealed this

Sixteenth Day of October, 1990

Attest:

HARRY F. MANBECK, JR.

Attesting Officer

Commissioner of Patents and Trademarks